US012586662B2

(12) United States Patent
Maeda

(10) Patent No.: US 12,586,662 B2
(45) Date of Patent: Mar. 24, 2026

(54) BIOLOGICAL MATERIAL ANALYSIS METHOD, BIOLOGICAL MATERIAL ANALYSIS DEVICE, AND BIOLOGICAL MATERIAL ANALYSIS PROGRAM

(71) Applicant: FUJIFILM Corporation, Tokyo (JP)

(72) Inventor: Kiyohiro Maeda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1653 days.

(21) Appl. No.: 16/538,396

(22) Filed: Aug. 12, 2019

(65) Prior Publication Data

US 2019/0362811 A1 Nov. 28, 2019

Related U.S. Application Data

(63) Continuation of application No. PCT/JP2018/003207, filed on Jan. 31, 2018.

(30) Foreign Application Priority Data

Feb. 14, 2017 (JP) ................................. 2017-024633

(51) Int. Cl.
| | |
|---|---|
| *G16B 40/00* | (2019.01) |
| *G16B 5/30* | (2019.01) |
| G16B 45/00 | (2019.01) |

(52) U.S. Cl.
CPC ............... *G16B 40/00* (2019.02); *G16B 5/30* (2019.02); *G16B 45/00* (2019.02)

(58) Field of Classification Search
CPC .................................. G16B 40/00; G16B 5/30
See application file for complete search history.

(56) References Cited

U.S. PATENT DOCUMENTS

| | | |
|---|---|---|
| 2009/0112479 A1 | 4/2009 | Kawai et al. |
| 2009/0112480 A1 | 4/2009 | Kim et al. |
| 2011/0246080 A1 | 10/2011 | Polouliakh et al. |
| 2014/0206962 A1 | 7/2014 | Tanii |
| 2015/0302165 A1 | 10/2015 | Aihara et al. |

FOREIGN PATENT DOCUMENTS

| | | |
|---|---|---|
| CN | 103476337 A | 12/2013 |
| CN | 105009130 A | 10/2015 |
| EP | 1 912 130 A1 | 4/2008 |
| JP | 2003-141123 A | 5/2003 |
| JP | 2004-240541 A | 8/2004 |
| JP | 2005-149196 A | 6/2005 |
| JP | 2007-52766 A | 3/2007 |
| JP | 2007-312653 A | 12/2007 |
| JP | 2016-024655 A | 2/2016 |
| WO | WO 2004/048532 A2 | 6/2004 |
| WO | WO 2010-064414 A1 | 6/2010 |

OTHER PUBLICATIONS

Chinese Office Action and Search Report for corresponding Chinese Application No. 201880011585.3, dated Nov. 17, 2022, with an English translation.
European Communication pursuant to Article 94(3) EPC for corresponding European Application No. 18754794.8, dated Oct. 4, 2022.
Heer et al., "Prefuse: A Toolkit for Interactive Information Visualization," CHI 2005, Conference on Human Factors in Computing Systems, Apr. 2-7, 2005, Portland, Oregon, USA, pp. 421-430, XP058137823.
Japanese Office Action issued on Oct. 20, 2020 in Japanese Patent Application No. 2018-568092, and an English machine translation.
Extended European Search Report for corresponding European Application No. 18754794.8. dated Jan. 31, 2020.
David Functional Annotation Bioinformatics Microarray Analysis, URL: https://david.nciforf.gov, 2 pages; access date Jul. 1, 2019.
Fang et al., "Transcriptome Analysis of Early Organogenesis in Human Embryos", Developmental Cell, vol. 19, Jul. 20, 2010, pp. 174-184 (11 pages).
Fang et al., "Transcriptome Profiles of Early Organogenesis in Human Embryos and Integrative Mining for Underlying Molecular Network", Gene Expression Omnibus, URL: http://www.ncbi.nlm.nih.gov/geo/query/acc.cgi?acc=GSE18887, 2010, 2 pages.
Gene Ontology Resource, URL: http://www.geneontology.org/, Jul. 1, 2019, 2 pages; access date Jul. 1, 2019.
International Preliminary Report on Patentability and Written Opinion of the International Searching Authority(Forms PCT/IB/326, PCT/IB/373 and PCT/ISA/237), dated Aug. 29, 2019, for International Application No. PCT/JP2018/003207, with an English Translation.
International Search Report (Form PCT/ISA/210), dated Feb. 27, 2018, for International Application No. PCT/JP2018/003207, with an English translation.
Sign: Large-Scale Gene Network Estimation Software, URL: http://sign.hgc.jp/, 2019, 2 pages; access date Jul. 1, 2019.
European Summons to Attend Oral Proceedings Pursuant to Rule 115(1) EPC for corresponding European Application No. 18 754 794.8, dated Jul. 4, 2025.
European Decision to Refuse a European Patent Application for corresponding European Application No. 18 754 794.8, dated Jan. 7, 2026.

*Primary Examiner* — Jerry Lin
(74) *Attorney, Agent, or Firm* — Birch, Stewart, Kolasch & Birch, LLP

(57) ABSTRACT

Time-series data formed by acquiring values indicating amounts or states of a plurality of biological materials for each biological material at a plurality of time points is prepared, the plurality of biological materials are divided into a plurality of groups on the basis of temporal variations of time-series data of the respective biological materials, representative time-series data indicating a state of each group is generated on the basis of time-series data of at least one biological material included in each group, and dependencies between the groups are estimated on the basis of the representative time-series data of each group.

12 Claims, 13 Drawing Sheets

TEMPORAL
VARIATION

BIOLOGICAL
FUNCTION

GROUP 1_1

GROUP 1

GROUP 1_2

GROUP 1_3

GROUP 2_1

GROUP 2

GROUP 2_2

GROUP X

GROUP Y

GROUP Z

VALUE

TIME POINT

BIOLOGICAL MATERIAL ANALYSIS METHOD, BIOLOGICAL MATERIAL ANALYSIS DEVICE, AND BIOLOGICAL MATERIAL ANALYSIS PROGRAM

CROSS-REFERENCE TO RELATED APPLICATIONS

This application is a continuation application of International Application No. PCT/JP2018/003207 filed Jan. 31, 2018, the disclosure of which is incorporated herein by reference in its entirety. Further, this application claims priority from Japanese Patent Application No. 2017-024633 filed Feb. 14, 2017, the disclosure of which is incorporated herein by reference in its entirety.

BACKGROUND OF THE INVENTION

1. Field of the Invention

The present disclosure relates to a biological material analysis method, a biological material analysis device, and a biological material analysis program for estimating dependencies when a plurality of biological materials function in vivo.

2. Description of the Related Art

Multiple genes (more than tens of thousands in a human) are present as ribonucleic acid (RNA) and protein in vivo. The amount or state of genes (for example, chemical modification) varies over time while depending on each other.

Further, since the genes show functions in vivo through the dependencies, for example, in a case where cells are treated using a medicine or the like, it is possible to clarify an action mechanism of the medicine by analyzing which dependencies the amount or state of genes change over time in.

Here, WO2010/064414A (Patent Document 1) discloses a method for grouping multiple genes on the basis of similarities in temporal variations of expression levels. Further, US2009/0112480A (Patent Document 2) discloses a method for grouping multiple genes on the basis of similarities of expression data and similarities of biological functions associated therewith.

However, WO2010/064414A and US2009/0112480A do not propose any method for checking dependencies of expression levels of multiple genes. Only by grouping the multiple genes, it is difficult to understand the action mechanism of the medicine or the like as described above.

WO2004/048532A (Patent Document 3) discloses a method for estimating, from time-series data of expression levels of multiple genes, dependencies of the genes.

SUMMARY OF THE INVENTION

However, in the method disclosed in WO2004/048532A, in a case where the number of measurement time points of data is smaller than the number of genes which are analysis targets, there is a problem in that its estimation result is not easily settled. Since it costs money and efforts to measure expression levels of genes at multiple time points, there is even a case where the number of measurement time points of is smaller than the number of genes by more than one digit. In such a case, there are many cases where the estimation result is not determined.

Such a problem occurs due to the following reason. In a case where the number of measurement time points of time-series data is smaller than the number of genes, as a range of the number becomes large, a situation where time-series data of a plurality of genes shows approximately the same temporal variation easily occurs. Thus, in an algorithm for estimating dependencies of the time-series data, it is difficult to distinguish the plurality of genes from each other, and thus, it is difficult to determine its estimation result.

The present disclosure has been made in consideration of the above-mentioned problems, and an object of the invention is to provide a biological material analysis method, a biological material analysis device, and a biological material analysis program for easily determining estimation results, in a case where dependencies of biological materials are estimated on the basis of time-series data obtained by measuring the amount of multiple biological materials or state values thereof at multiple time points, even in a case where the number of measurement time points of the data is smaller than the number of biological materials.

According to an aspect of the present disclosure, there is provided a biological material analysis method comprising: preparing time-series data formed by acquiring values indicating amounts or states of a plurality of biological materials for each of the biological materials at a plurality of time points; dividing the plurality of biological materials into a plurality of groups on the basis of a temporal variation of the time-series data of each of the biological materials; generating representative time-series data indicating a state of each group through computation on the basis of the time-series data of at least one biological material included in each group; and estimating a dependency between the groups through computation on the basis of the representative time-series data of each group.

In the biological material analysis method according to this aspect of the present disclosure, the plurality of biological materials may be divided into a plurality of groups on the basis of a similarity of temporal variations of time-series data of the respective biological materials and a similarity of biological functions of the respective biological materials.

In the biological material analysis method according to this aspect of the present disclosure, the similarity of the biological functions of the respective biological materials may be evaluated on the basis of a gene ontology of each of the biological materials, a canonical passway of each biological material, an upstream factor of each of the biological materials, an expression system of each of the biological materials, or a disease relating to each of the biological materials.

In the biological material analysis method according to this aspect of the present disclosure, in a case where the plurality of biological materials are divided into the plurality of groups, at least one biological material may be allowed to belong to a plurality of groups.

The biological material analysis method according to this aspect of the present disclosure may further comprise: preparing a plurality of pieces of reference time-series data in advance; and comparing the plurality of pieces of reference time-series data with the time-series data of the respective biological materials to divide the plurality of biological materials into the plurality of groups.

In the biological material analysis method according to this aspect of the present disclosure, in a case where the dependency between the groups is estimated, representative time-series data of each group may be expressed as a function of representative time-series data of another group.

In the biological material analysis method according to this aspect of the present disclosure, in a case where the dependency between the groups is estimated, a value of the representative time-series data of each group at a first time point may be set as a function of a value of the representative time-series data of the other group at a second time point before the first time point.

In the biological material analysis method according to this aspect of the present disclosure, in a case where the dependency between the groups is estimated, the representative time-series data of each group may be expressed as a conditional probability or a conditional probability density function of the representative time-series data of the other group.

In the biological material analysis method according to this aspect of the present disclosure, the representative time-series data of each group may be set as an average value, a median value, a mode, a variance, a standard deviation, or a triple or higher moment of values of time-series data of biological materials that belong to each group at respective time points.

In the biological material analysis method according to this aspect of the present disclosure, a value indicating the amount of the biological material may be a value indicating an expression level, an existence amount, a concentration, or a density of the biological material.

In the biological material analysis method according to this aspect of the present disclosure, a value indicating the state of the biological material may be a value indicating the presence or absence of expression of the biological material, a value indicating the presence or absence of existence thereof, a value indicating the presence or absence of chemical modification thereof, or a value indicating a ratio between biological materials having chemical modification and biological materials without chemical modification.

In the biological material analysis method according to this aspect of the present disclosure, the plurality of biological materials may include at least one of deoxyribonucleic acid (DNA), ribonucleic acid (RNA), protein, or low molecular compounds in vivo.

The biological material analysis method according to this aspect of the present disclosure may further comprise: generating a network diagram in which the respective groups are expressed as nodes and nodes corresponding to groups having the dependency are connected through edges.

In the biological material analysis method according to this aspect of the present disclosure, character information or a diagram relating to a biological function of a group corresponding to each of the nodes, a diagram indicating a name, a sign, a structure or a composition of a biological material included in the group corresponding to each of the nodes, or character information relating to the biological material may be additionally displayed in the network diagram.

The biological material analysis method according to this aspect of the present disclosure may further comprise: receiving selection of the node included in the network diagram; and additionally displaying character information or a diagram relating to a biological function of a group corresponding to the selected node, a diagram indicating a name, a sign, a structure or a composition of a biological material included in the group corresponding to the selected node, or character information relating to the biological material in the network diagram.

According to another aspect of the present disclosure, there is provided a biological material analysis device comprising: a storage that stores time-series data formed by acquiring values indicating amounts or states of a plurality of biological materials for each of the biological materials at a plurality of time points; a classifier that divides the plurality of biological materials into a plurality of groups on the basis of a temporal variation of time-series data of each of the biological materials; and a dependency estimator that generates representative time-series data indicating the state of each group on the basis of time-series data of at least one biological material included in each group, and estimates a dependency between the groups on the basis of the representative time-series data of each group.

According to still another aspect of the present disclosure, there is provided a biological material analysis program for causing a computer to execute: a step of storing time-series data formed by acquiring values indicating amounts or states of a plurality of biological materials for each of the biological materials at a plurality of time points; a step of dividing the plurality of biological materials into a plurality of groups on the basis of a temporal variation of the time-series data of each of the biological materials; and a step of generating representative time-series data indicating a state of each group on the basis of the time-series data of at least one biological material included in each group, and estimating a dependency between the groups on the basis of the representative time-series data of each group.

According to the biological material analysis method, the biological material analysis device, and the biological material analysis program of the present disclosure, time-series data formed by acquiring values indicating amounts or states of a plurality of biological materials for each of the biological materials at a plurality of time points is stored, the plurality of biological materials are divided into a plurality of groups on the basis of a temporal variation of the time-series data of each of the biological materials. Further, representative time-series data indicating a state of each group is generated on the basis of the time-series data of at least one biological material included in each group, and a dependency between the groups is estimated on the basis of the representative time-series data of each group.

In a case where the plurality of biological materials are grouped on the basis of the temporal variation of the time-series data of each of the biological materials and the dependency between the groups is estimated, since ranges of the number of groups and the number of measurement time points are smaller than ranges of the number of biological materials and the number of measurement time points, it is possible to easily determine the estimation of the dependency.

DESCRIPTION OF THE PREFERRED EMBODIMENTS

Figure 1:
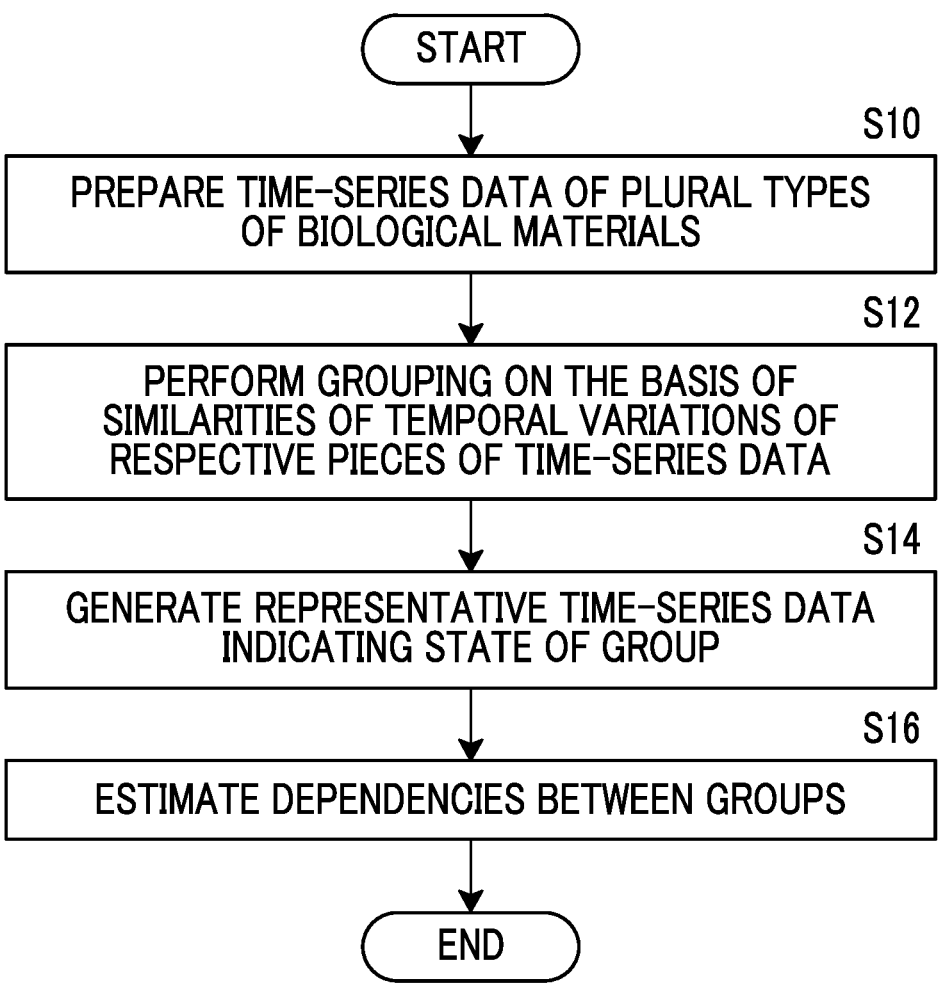
FIG. 1 is a flowchart for illustrating a first embodiment of a biological material analysis method of the present disclosure.

Hereinafter, a first embodiment of a biological material analysis method of the present disclosure will be described in detail with reference to the accompanying drawings. FIG. 1 is a flowchart for illustrating the biological material analysis method of this embodiment.

In the biological material analysis method of this embodiment, first, time-series data formed by acquiring values indicating amounts or states of a plurality of biological materials of each biological material at a plurality of time points is prepared (S10).

The plurality of biological materials include at least one of deoxyribonucleic acid (DNA), ribonucleic acid (RNA), protein, or low molecular compounds in vivo, for example. More specifically, the plurality of biological materials may be RNAs having different genes such as RNA of a gene A, RNA of a gene B, RNA of a gene C, and the like, or may be a combination of DNA and RNA, for example.

Further, as a value indicating the amount of a biological material, for example, an expression level, an existence amount, a concentration, a density, or the like of the biological material may be used. In addition, as a value indicating the state of the biological material, a value indicating the presence or absence of expression of the biological material, a value indicating the presence or absence of existence thereof, a value indicating the presence or absence of chemical modification, or a ratio between of biological materials having chemical modification and biological materials without chemical modification may be used.

As the value indicating the presence or absence of expression of the biological material, the value indicating the presence or absence of existence thereof, and the value indicating the presence or absence of chemical modification, a value indicating "presence" and a value indicating "absence" are respectively set in advance. For example, the value indicating "presence" is set to "1", and the value indicating "absence" is set to "0". Further, the presence or absence of chemical modification may include the presence or absence of phosphorylation, the presence or absence of methylation, or the like, for example.

The values indicating the amounts or states of the plurality of biological materials may be acquired through microarray measurement or the like, or may be prepared by acquiring data stored in a known database or the like through the Internet or the like, for example. As such a database, Gene Expression Omnibus may be used, for example. More specifically, data obtained by measuring gene expression in an organ development process in human embryos (see ncbi.nlm.nih.gov/geo/query/acc.cgi?acc=GSE18887) may be used. The data is acquired by Fang or the like (Dev Cell, 19(1): 174-84, 2010).

Figure 2:
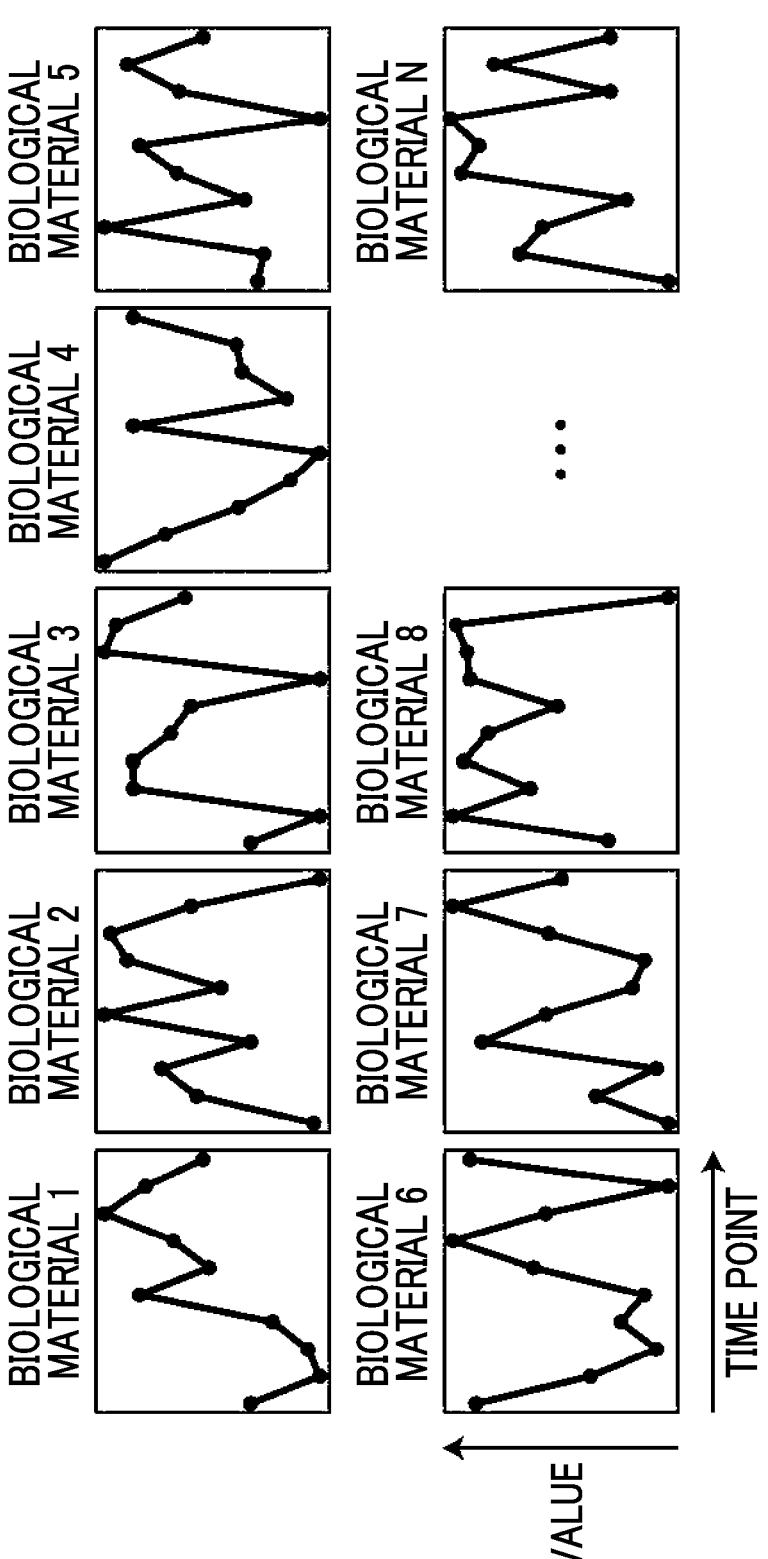
FIG. 2 is a diagram showing an example of time-series data of each biological material.

The values indicating the amounts or states of the plurality of biological materials are measured in time series at a plurality of time points, and are acquired as time-series data. FIG. 2 is a diagram showing an example of time-series data acquired for each of biological materials 1 to N.

Figure 3:
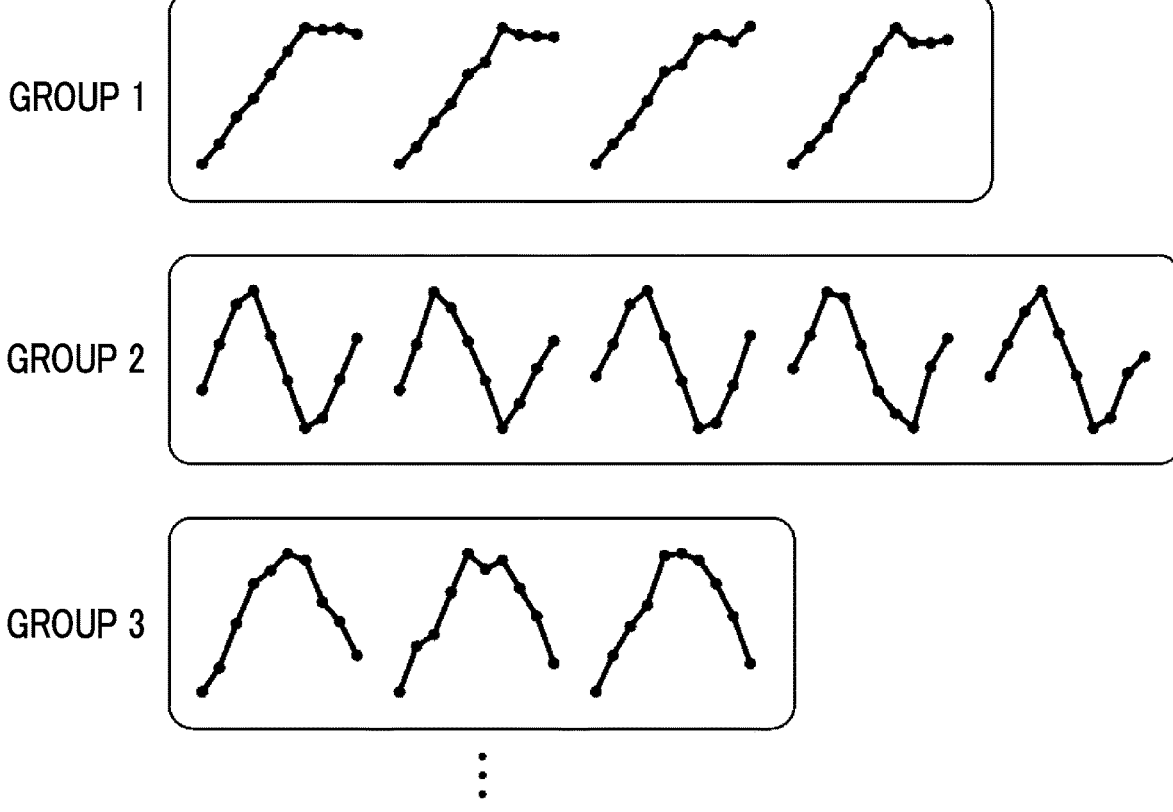
FIG. 3 is a diagram for illustrating grouping of a plurality of pieces of time-series data.

Next, in the biological material analysis method of this embodiment, the plurality of biological materials are divided into a plurality of groups on the basis of similarities of temporal variations of time-series data of the respective biological materials as shown in FIG. 2 (S12). Specifically, as shown in FIG. 3, by collecting time-series data of which temporal variations are similar to each other as one group, biological materials corresponding to the similar time-series data are collected as one group. With respect to the similarities of time-series data, for example, similarity levels or the like of respective pieces of time-series data may be calculated, and time-series data of which similarity levels are equal to or greater than a predetermined threshold may be collected as one group.

Figure 4:
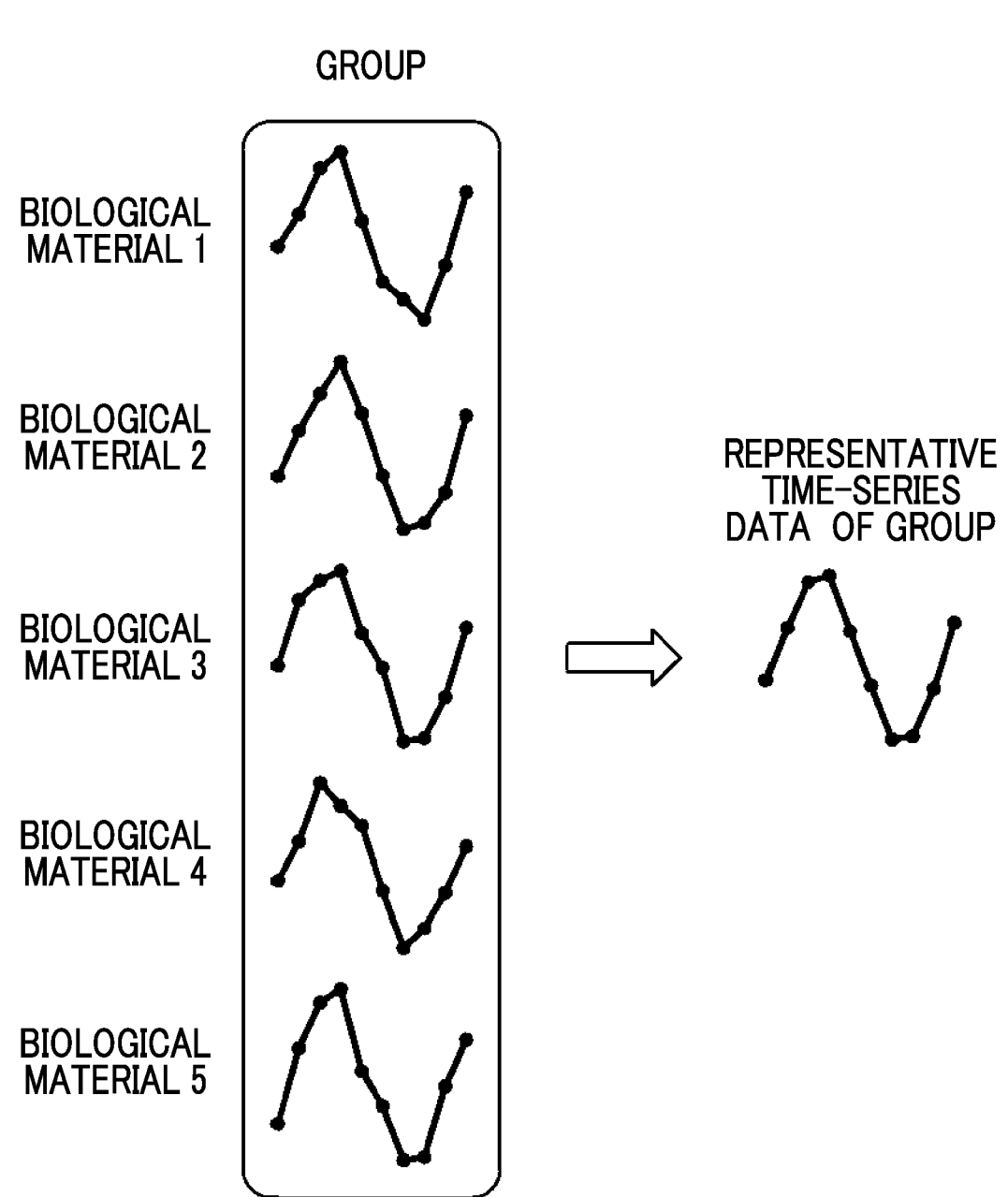
FIG. 4 is a diagram for illustrating a method for acquiring one piece of representative time-series data on the basis of time-series data of a plurality of biological materials included in a group.

As described above, after the plurality of biological materials are divided into the plurality of groups, representative time-series data indicating a state of each group is generated through computation on the basis of time-series data of at least one biological material included in each group (S14). FIG. 4 is a diagram for illustrating a method for acquiring one piece of representative time-series data on the basis of time-series data from a biological material 1 to a biological material 5 included in one group.

The representative time-series data of the group may be generated by calculating, for example, an average value, a median value, a mode, a variance, a standard deviation, or a triple or higher moment of values, at respective time points, of time-series data of biological materials that belong to the group. Specifically, in the case of the example shown in FIG. 4, the representative time-series data may be generated by calculating an average value of values, at a first time point, of the respective pieces of time-series data of the biological material 1 to the biological material 5 to become a first time point value of the representative time-series data, calculating an average value of values, at a second time point, of the respective pieces of time-series data to become a second time point value of the representative time-series data, and similarly, calculating an average value of values, at an n-th time point, of the respective pieces of time-series data to become an n-th time point value of the representative time-series data.

Then, in the biological material analysis method of this embodiment, dependencies between the groups are estimated through computation on the basis of the representative time-series data of each group generated as described above (S16).

Figure 5:
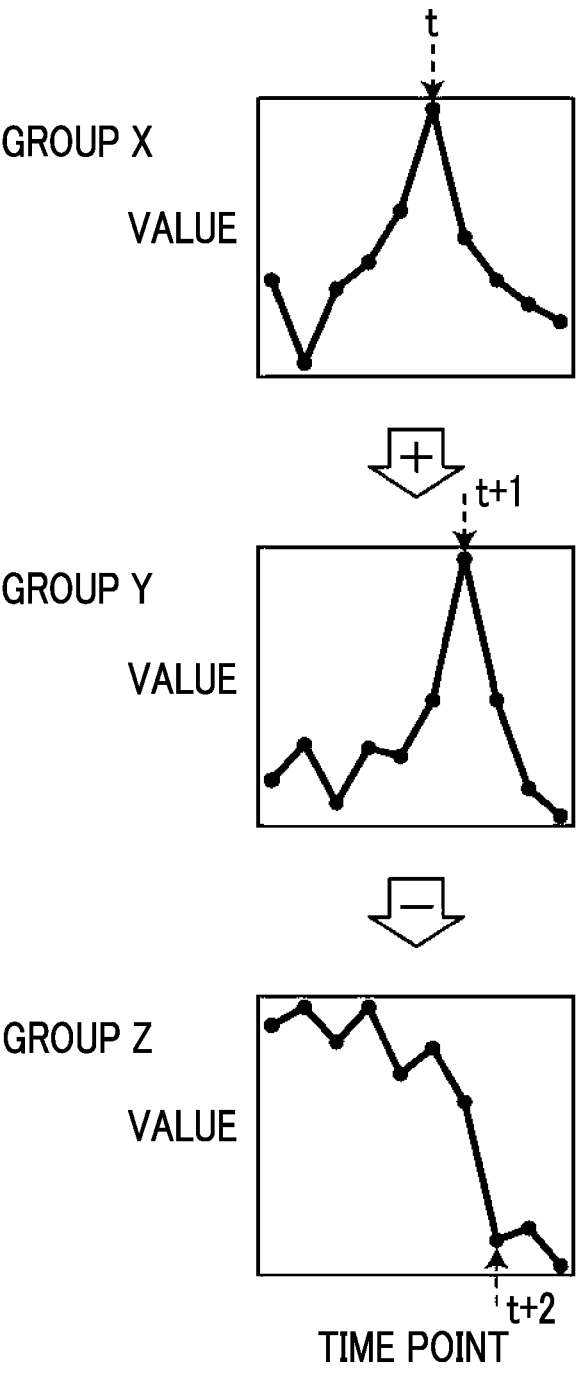
FIG. 5 is a conceptual diagram for illustrating a method for estimating dependencies of groups on the basis of representative time-series data of the groups.

Here, a method for estimating the dependencies between the groups on the basis of the representative time-series data of the groups will be conceptually described with reference to FIG. 5. FIG. 5 shows representative time-series data of a group X, a group Y, and a group Z, respectively. Further, in the representative time-series data of the group X, a value at a time point t becomes maximum, and in the representative time-series data of the group Y, a value at a time point t+1 becomes maximum. That is, as the value of the representative time-series data of the group X becomes a maximum value, the representative time-series data of the group Y increases and becomes a maximum value. Further, after the value of the representative time-series data of the group X becomes maximum at the time point t+1, the value of the representative time-series data of the group Z greatly decreases at a time point t+2.

In this way, in a case where it is estimated that representative time-series data of a first group and representative time-series data of a second group are changed in association, it is estimated that the first group and the second group have a dependency.

Figure 6A:
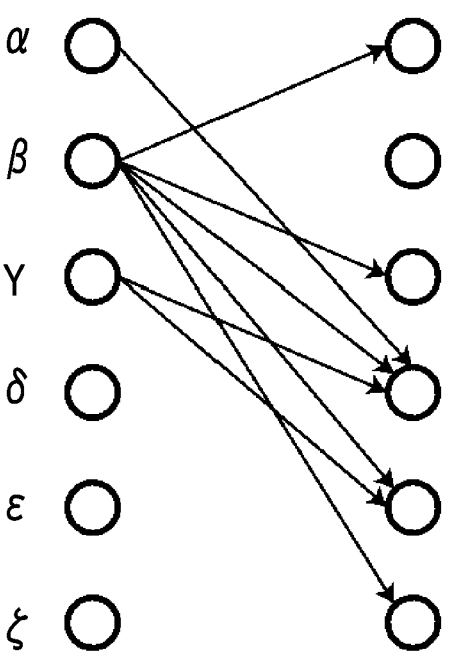
FIGS. 6A and 6B are diagrams for schematically illustrating a method for estimating dependencies based on the Bayesian network scheme.
Figure 6B:
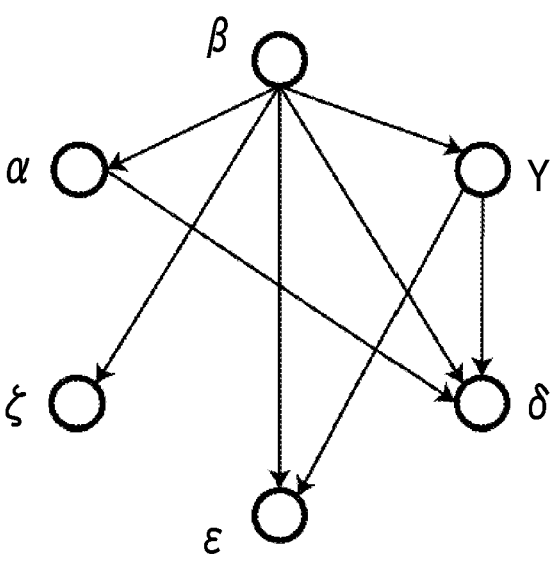

The above-described dependencies between the groups may be modeled by setting a value, at a first time point (time t), of representative time-series data of each group as a function of a value, at a second time point (time t−1) before the first time point, of representative time-series data of another group, as shown in FIGS. 6A and 6B. Thus, a form that a state of each group at a specific time point depends on a previous state of another group may also be expressed. α to ζ shown in FIG. 6A represent respective groups. For example, in a case where representative time-series data of another group at a time point t is changed in accordance with a variation of representative time-series data of the group α at a time point t−1, it is estimated that the group α and another group have a dependency. In the example shown in FIG. 6A, it is estimated that the group a depends on the group β, the group γ depends on the group β, the group δ depends on the groups α, β, and γ, the group ε depends on the groups β and γ, and the group ζ depends on the group β. In this way, a form that a state of each group at a specific time point depends on a previous state of another group may also be expressed.

Further, as described above, in a case where a value of representative time-series data of each group is expressed as a function of a value of representative time-series data of another group, the value of the representative time-series data of each group may be expressed as a conditional probability or a conditional probability density function of the representative time-series data of the other group. Since noise is included in data that shows description of behaviors of biological materials, it is possible to perform estimation based on occurrences in vivo using description based on probabilities.

In this embodiment, an example in which dependencies between groups are modeled by the Bayesian network scheme for estimation is shown, but the present disclosure is not limited thereto, and the modeling may be performed by other known methods, for example, the Boolean network scheme, a differential equation system, or the like.

FIG. 6B is a diagram showing an example of a network diagram in which respective groups are expressed as nodes, in which nodes corresponding to groups having dependencies are connected through edges. The network diagram shown in FIG. 6B may be displayed by a display device or the like, for example. By displaying the network diagram in this way, a user can easily understand the dependencies.

According to the biological material analysis method of this embodiment, a plurality of biological materials are grouped on the basis of a temporal variation of time-series data of each biological material, and dependencies between the groups are estimated. Thus, ranges of the number of groups and the number of measurement time points are smaller than ranges of the number of biological materials and the number of measurement time points, and thus, it is possible to easily determine estimation of dependencies.

Figure 7:
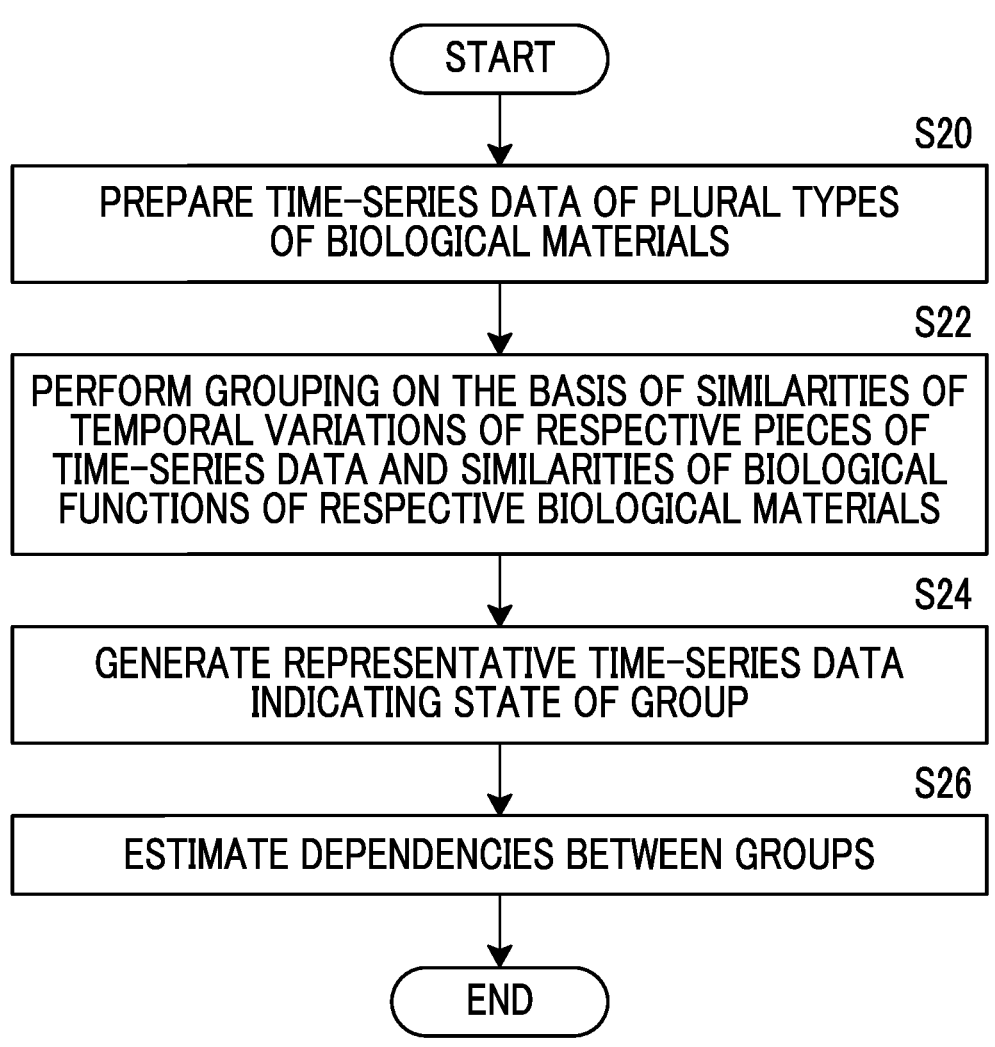
FIG. 7 is a flowchart for illustrating a second embodiment of the biological material analysis method of the present disclosure.

Next, a second embodiment of the biological material analysis method of the present disclosure will be described. FIG. 7 is a flowchart for illustrating the biological material analysis method of this embodiment. In the biological material analysis method of the first embodiment, a plurality of biological materials are grouped on the basis of similarities of temporal variations of time-series data of the respective biological materials, but in the second embodiment, grouping is performed in further consideration of similarities of biological functions of respective biological materials (S22).

Figure 8:
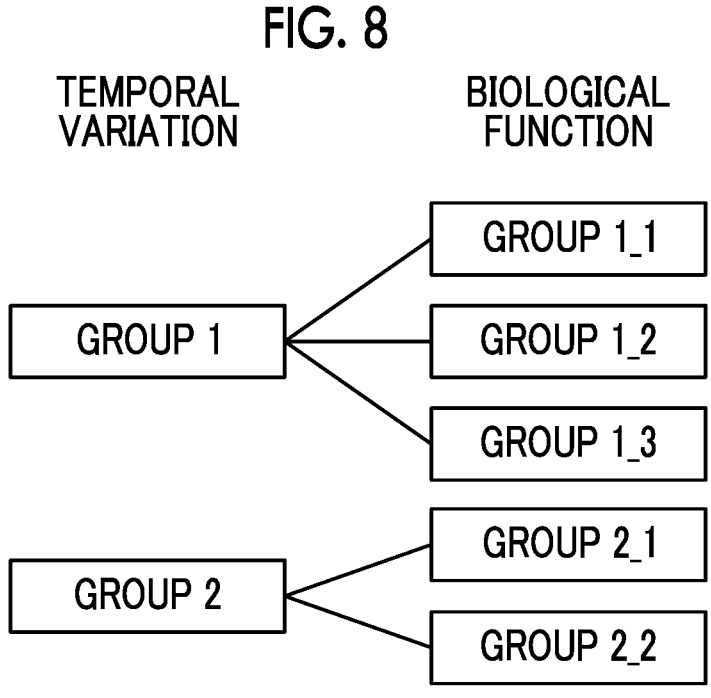
FIG. 8 is a diagram for illustrating a method for performing grouping on the basis of a similarity of temporal variations of time-series data of respective biological materials, and a similarity of biological functions of the respective biological materials.

For example, as shown in FIG. 8, on the basis of similarities of temporal variations of time-series data of respective biological materials, the biological materials are grouped into a group 1 and a group 2. Then, on the basis of similarities of biological functions of respective biological materials that belong to the group 1 the group 1 is divided into a group 1_1, a group 1_2, and a group 1_3, and the group 2 is divided into a group 2_1 and a group 2_2.

Evaluation of the similarities of the biological functions of the respective biological materials may be performed on the basis of whether the biological materials have a common gene ontology, whether the biological materials belong to a canonical passway, whether the biological materials have a common upstream factor, whether the biological materials relate to a common expression system, or whether the biological materials relate to a common disease, for example.

Figure 9:
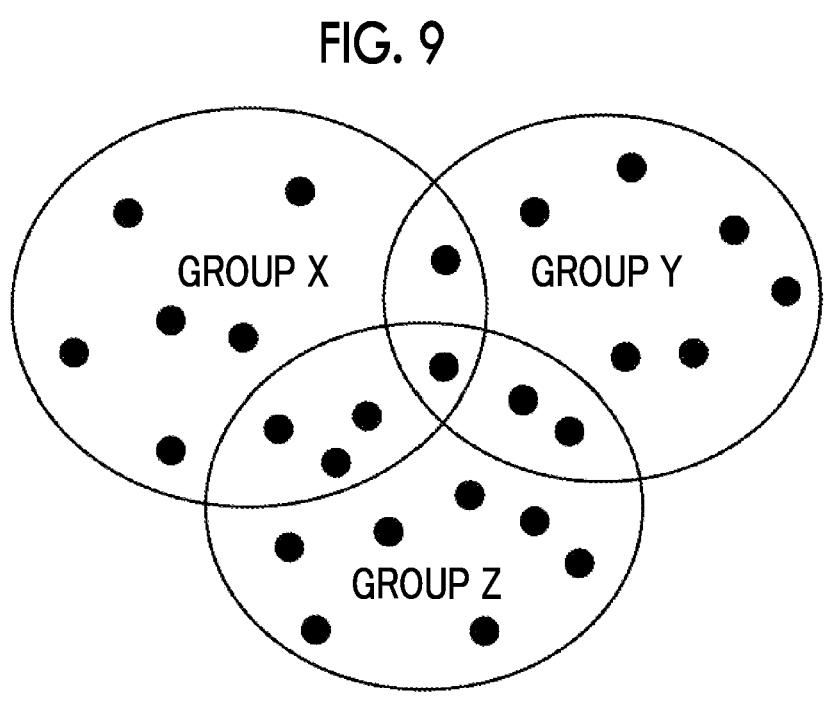
FIG. 9 is a diagram for illustrating a state where one biological material is allowed to belong to a plurality of groups.

As described above, in a case where a plurality of biological materials are grouped on the basis of similarities of temporal variations of time-series data of respective biological materials and similarities of biological functions of the respective biological materials, at least one biological material may be allowed to belong to a plurality of groups. FIG. 9 is a diagram for illustrating an example in which one biological material belongs to a plurality of groups. One black circle shown in FIG. 9 represents one biological material. In the example shown in FIG. 9, a biological material that belongs to two groups and a biological material that belongs to three groups are present.

There is a case where biological materials relate to a plurality of biological functions. As described above, by allowing one or more biological materials to belong to two or more groups, it is possible to obtain an estimation result based on actual occurrences in vivo.

The biological material analysis method of the second embodiment is the same as the biological material analysis method of the first embodiment in terms of steps (S20, S24, and S26 in FIG. 7) other than the step of performing the grouping using the similarities of the biological functions of the respective biological materials as described above.

As in the biological material analysis method of the first embodiment, in a case where grouping is performed on the basis of only similarities of temporal variations of time-series data of respective biological materials, multiple biological materials are collected to a relatively small number of groups. Thus, even in a case where dependencies between groups are estimated, there is a case where a sufficient effect cannot be obtained, for example, for the purpose of detecting an action mechanism of a medicine or the like. According to the biological material analysis method of the second embodiment, since a plurality of biological materials are groups on the basis of similarities of variations of time-series data and similarities of biological functions, it is possible to alleviate or solve the above-mentioned problems.

Further, even in a case where dependencies between biological materials are estimated, there is a case where it is difficult for a human to understand its biological meaning. In this regard, as in the biological material analysis method of the second embodiment, in a case where biological materials are grouped on the basis of similarities of biological functions and dependencies between groups are estimated, it is possible to analyze an estimation result in a function unit, to thereby easily understand the estimation result.

Figure 10:
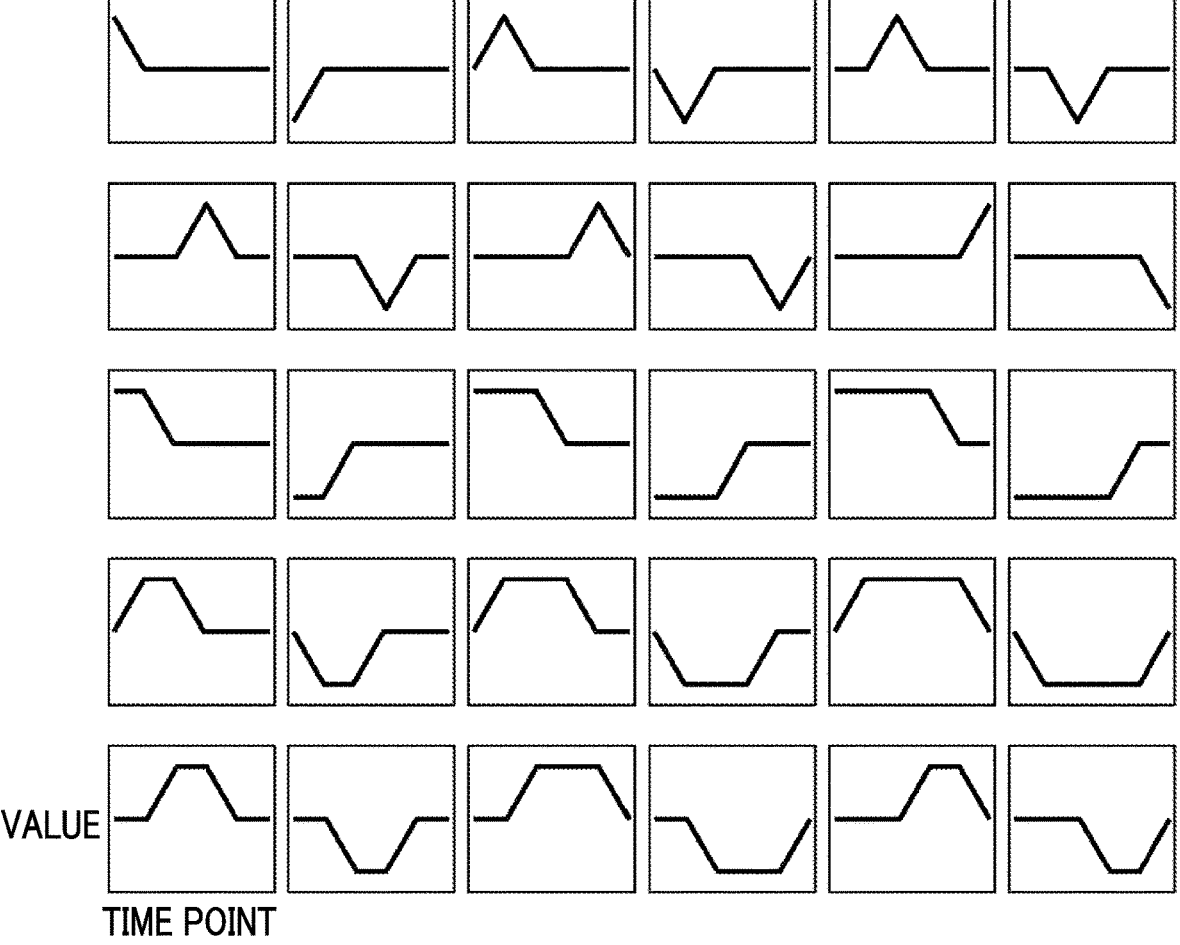
FIG. 10 is a diagram showing an example of reference time-series data that is set in advance.

In the biological material analysis methods of the above-described embodiments, a plurality of biological materials are grouped by calculating similarities of time-series data of respective biological materials, but the grouping method is not limited thereto. For example, as shown in FIG. 10, a method for preparing multiple pieces of reference time-series data in advance and comparing the reference time-series data with time-series data of respective biological materials to divide the plurality of biological materials into a plurality of groups may be used. That is, grouping may be performed so that biological materials corresponding to time-series data similar to the same reference time-series data belong to the same group.

Figure 11:
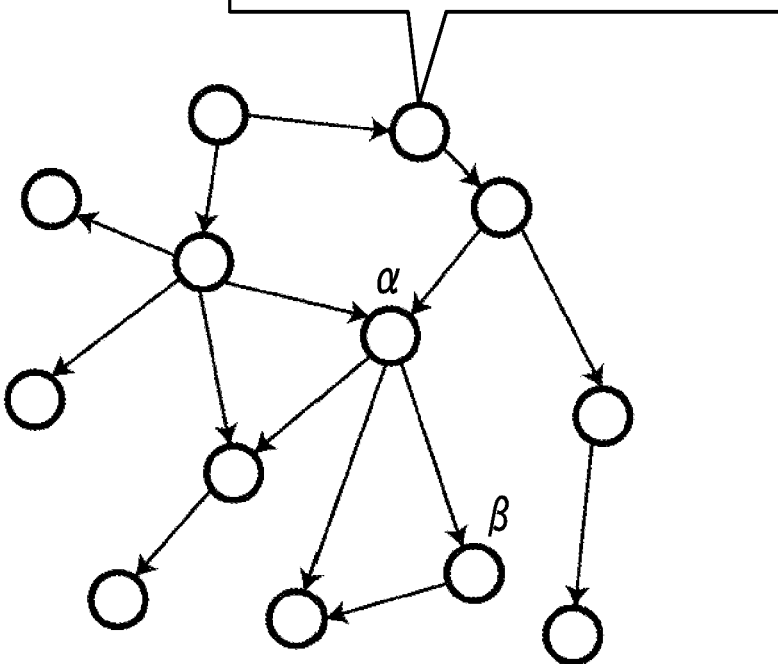
FIG. 11 is a diagram showing an example in which a name of a group and names of biological materials thereof are additionally displayed with respect to a network diagram.

Further, in a case where the network diagram shown in FIG. 6B is displayed in a display device, with respect to nodes corresponding to respective groups as shown in FIG. 11, a name of each group and names of biological materials that included in the group may be displayed. Further, in addition to the names of the biological materials, character information relating to the biological materials, signs indicating the biological materials, diagrams indicating structures of the biological materials or compositions of the biological materials, or the like may be additionally displayed in the network diagram. In addition, character information, a diagram, or the like relating to a biological function common to biological materials included in a group may be additionally displayed in the network diagram.

As described above, in displaying the name of each group, or the like, in a case where the number of nodes is large, and in a case where the names of the groups, or the like are displayed with respect to all the nodes, it may be difficult to find out the names. Accordingly, a method for receiving an input command from an input device such as a mouse or a keyboard to receive selection of a node included in the network diagram, and additionally displaying a name of a group, names of biological materials, or the like, with respect to only the selected node may be used. Thus, it is possible to display only user interested information, to thereby make the network diagram so as to be easily seen by a user.

Next, a specific example of the above-described biological material analysis method of the second embodiment will be described. Here, an example in which data obtained by measuring gene expression in an organ development process in human embryos is analyzed will be described.

First, the data obtained by measuring the above-mentioned gene expression is acquired from Gene Expression Omnibus that is a known database. The data is obtained by measuring expression of multiple genes at 6 time points of stages 9 to 14 among Carnegie stages (measure for step-dividing growth on the basis of morphological characteristics of embryos).

Values of amounts of expression of genes at the 6 time points are converted into differential values with respect to a temporal average for each gene and the values are normalized, so that time-series data for each gene is calculated.

Figure 12:
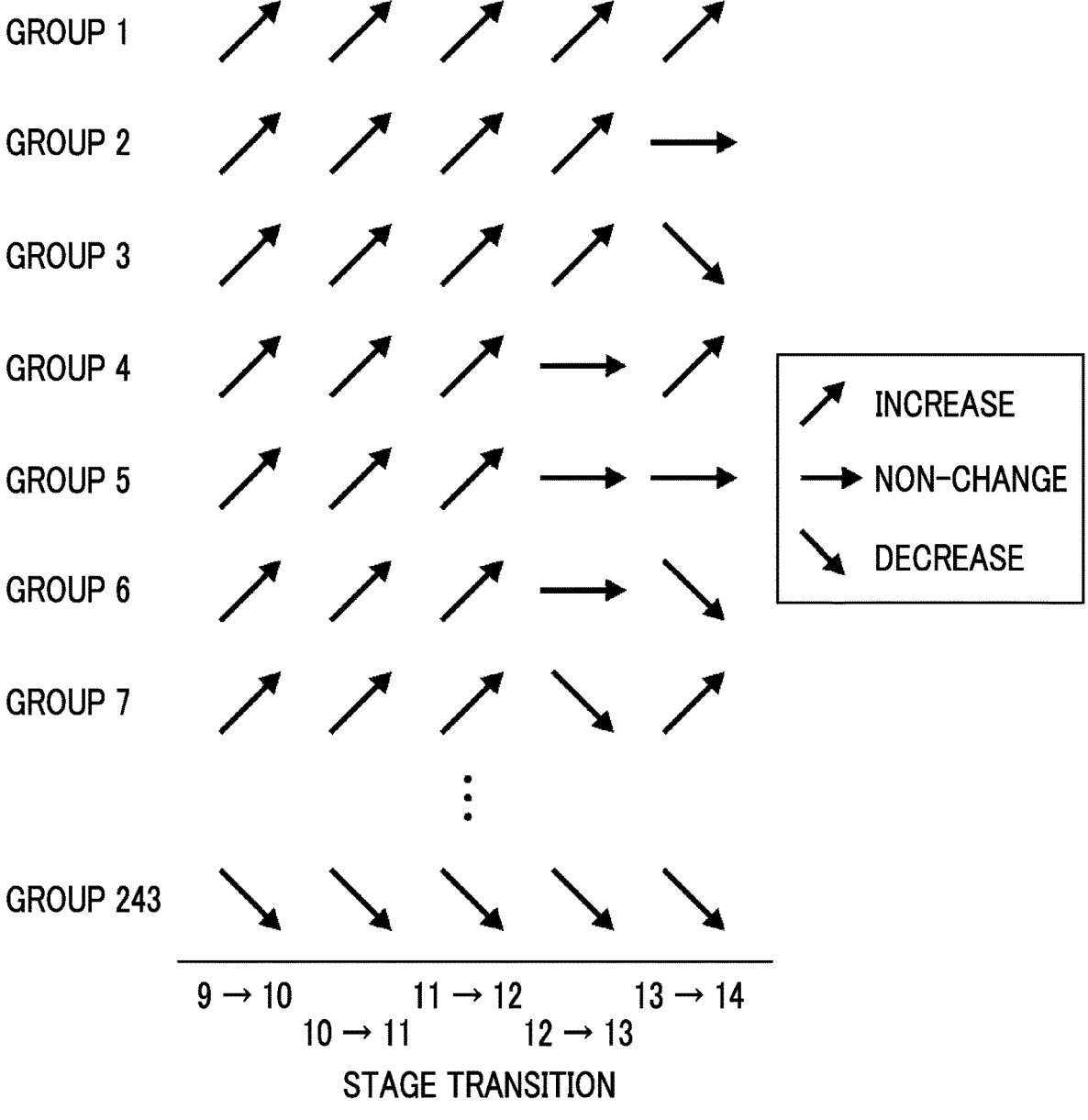
FIG. 12 is a diagram for illustrating a method for performing grouping on the basis of variations of values of time-series data at two adjacent time points.

Further, time-series data of which temporal variations are similar to each other is grouped. Specifically, it is determined whether a variation of value of time-series data at certain two adjacent time points (for example, two time points when the stage 9 transits to the stage 10) of five pairs of two adjacent time points indicates increase, non-change, or decrease, and thus, the time-series data is classified into 243 ($3^5$) groups as shown in FIG. 12. In this classification, time-series data that is determined as "non-change" at the entirety of five pairs of two adjacent time points is excluded from the following analysis.

Then, with respect to each of the respective groups that are classified as described above, as shown in FIG. 8, a plurality of genes included in each group are grouped by collecting genes of which biological functions are similar to each other. Specifically, genes having similar gene ontology terms (geneontology.org/) using functional annotation clustering of DAVID (david.ncifcrf.gov/) that is a common web tool are grouped. Here, genes allocated to two or more groups are allowed to be present.

In this way, grouping is performed on the basis of similarities of temporal variations of time-series data of respective genes and similarities of biological functions of the respective genes, and as a result, 468 groups are obtained.

Then, an average value of values, at respective time points, of time-series data of genes that belong to each group is calculated, so that representative time-series data of each group is generated.

Further, temporal dependencies between the representative time-series data of 468 groups are estimated using the Bayesian network scheme. Specifically, the dependencies are estimated by giving the representative time-series data of the 468 groups to SIGN-BN software (sign/hgc.jp/).

Figure 13:
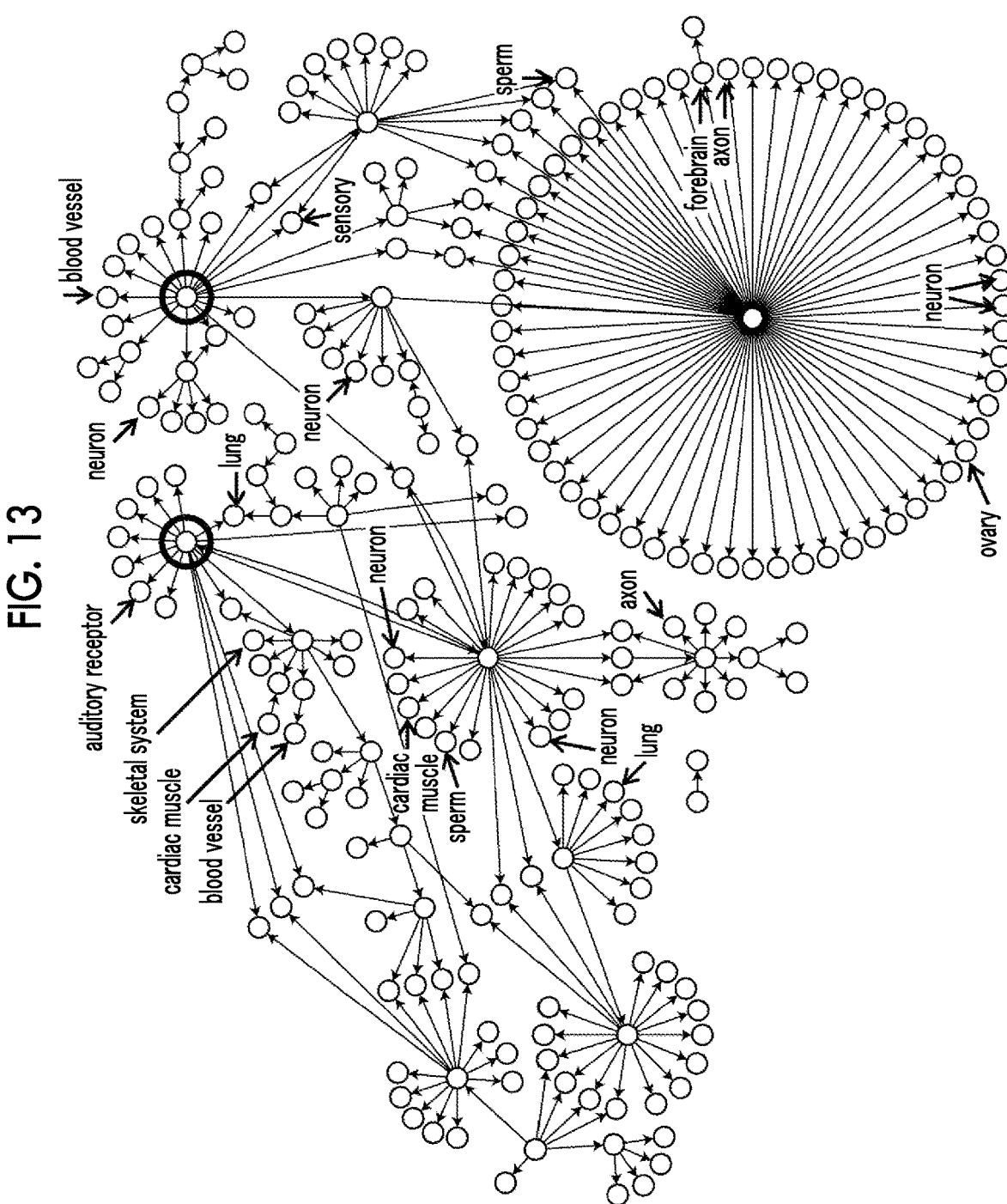
FIG. 13 is a diagram showing an example of a network diagram.

In addition, respective groups are represented as nodes on the basis of the estimated dependencies, and nodes having dependencies are connected to each other by edges to generate a network diagram as shown in FIG. 13. Thus, a hierarchic structure that matches a knowledge of developmental biology indicating that a small number of groups having a function for controlling organogenesis control states of multiple groups relating to formation of individual organs is obtained. In FIG. 13, two groups indicated by thick circles are present at the highest stream of the network, and mainly include genes of a transcription factor as members. 85% of the total groups are included downstream in the two groups, and it is shown that the small number of groups control the states of the multiple groups.

Figure 14:
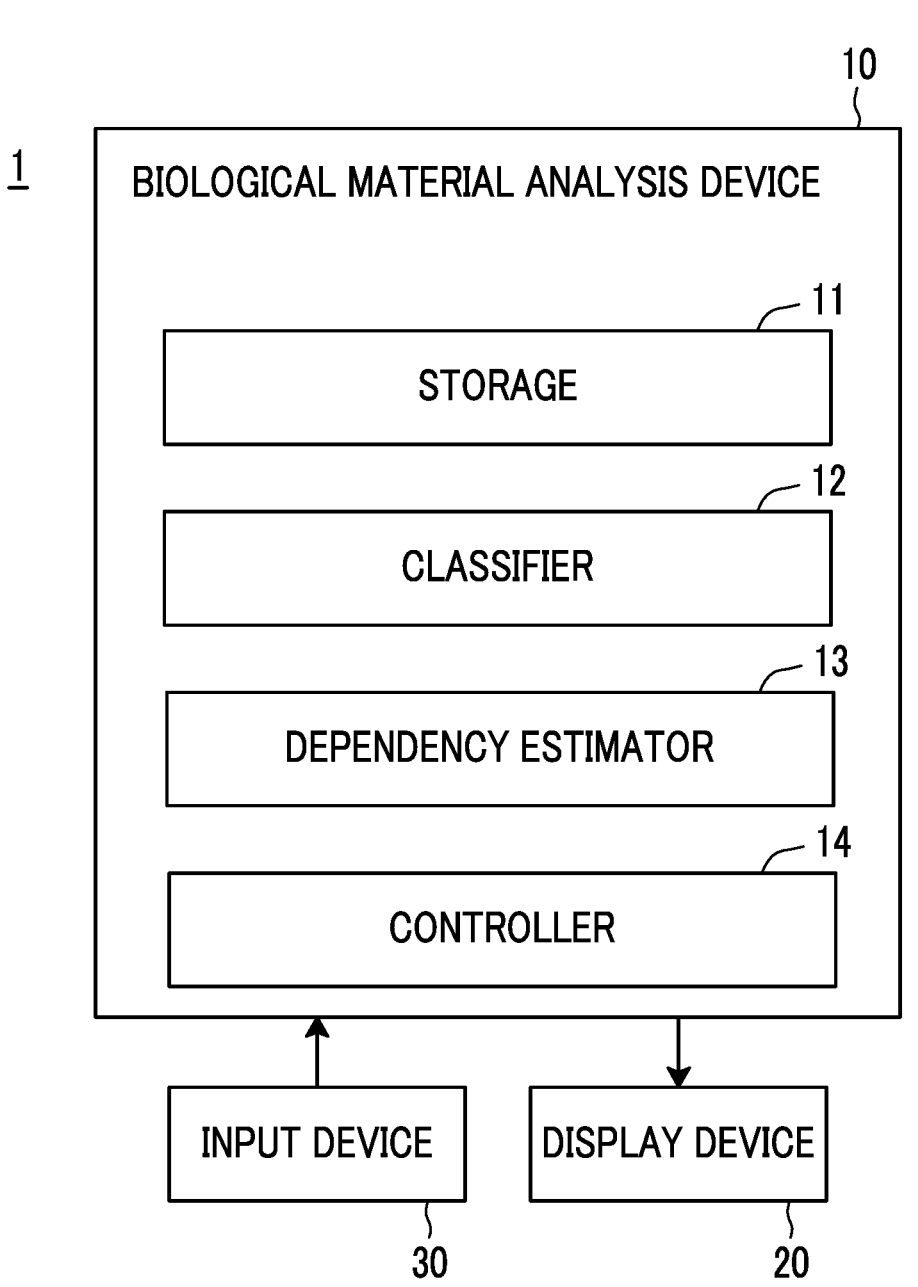
FIG. 14 is a block diagram showing a schematic configuration of a biological material analysis system using an embodiment of the biological material analysis device of the present disclosure.

A biological material analysis system used for executing the biological material analysis methods of the above-described first and second embodiments will be described. FIG. 14 is a block diagram showing a schematic configuration of a biological material analysis system 1 using an embodiment of the biological material analysis device of the present disclosure.

The biological material analysis system 1 includes a biological material analysis device 10, a display device 20, and an input device 30, as shown in FIG. 14.

The biological material analysis device 10 is configured of a computer that includes a central processing unit, a semiconductor memory, a hard disk, and the like. Further, an embodiment of a biological material analysis program of the present disclosure is installed in the hard disk. Further, as the biological material analysis program is executed by the central processing unit, a storage 11, a classifier 12, a dependency estimator 13, and a controller 14 shown in FIG. 1 perform their functions. Thus, a step of storing time-series data of each biological material as described above, a step of grouping a plurality of biological materials on the basis of a temporal variation of the time-series data of each biological material, a step of generating representative time-series data indicating a state of each group on the basis of time-series data of at least one biological material included in each group, and a step of estimating dependencies between the groups on the basis of the representative time-series data of the respective groups are executed by the computer.

The storage 11 is configured of a storage medium such as a semiconductor memory or a hard disk, and stores the above-described time-series data of each biological material.

The classifier 12 divides a plurality of biological materials into a plurality of groups on the basis of a temporal variation of time-series data of each biological material. The classifier 12 performs grouping using Functional Annotation Clustering of DAVID, as described above, for example. A specific grouping method is the same as the biological material analysis methods of the first and second embodiments. In a case where the biological material analysis method of the second embodiment is executed, it is assumed that biological functions of respective biological materials are set in advance in association with the respective biological materials and time-series data thereof.

The dependency estimator 13 generates representative time-series data indicating a state of each group on the basis of time-series data of at least one biological material included in each group, and estimates dependencies between the groups on the basis of the representative time-series data of the respective groups. The dependency estimator 13 estimates the dependencies between the groups using the above-described SiGN-BN software, for example. A specific method for estimating the dependencies between the groups is the same as the biological material analysis methods of the first and second embodiments.

The controller 14 is configured of a central processing unit, and generally controls the biological material analysis device 10.

The display device 20 is configured of a liquid crystal display, or the like, and displays the above-described network diagram or the like under the control of the controller 14.

The input device 30 is configured of a mouse, a keyboard, and the like, and receives selection of any node from a plurality of nodes included in the network diagram displayed on the display device 20. In a case where the selection of the node is received through the input device 30, a name of a group corresponding to the node, names of biological materials that are included in the group, and the like are displayed on the display device 20.

This application is based on Japanese Patent Application No. 2017-024633, and the entire disclosure thereof is incorporated herein by reference.

All documents, patent applications or technical standards disclosed in this specification are incorporated herein by reference to the same degree as in a case where referenced incorporation of each document, patent application or technical standard is specifically and individually disclosed.

What is claimed is:

1. A biological material analysis support-system comprising a biological material analysis device having a storage device, an input device, and a display device, wherein the biological material analysis device is configured to execute a process comprising:

preparing time-series data formed by acquiring, from a user via the input device or from the storage device, values indicating amounts or states of a plurality of biological materials for each of the biological materials at a plurality of time points;

dividing the plurality of biological materials into a plurality of groups on the basis of a temporal variation of the time-series data of each of the biological materials;

generating representative time-series data indicating a state of each group through computation on the basis of the time-series data of at least one biological material included in each group;

estimating a dependency between the groups through computation on the basis of the representative time-series data of each group;

generating a network diagram in which the respective groups are expressed as nodes and nodes corresponding to groups having the dependency are connected through edges, displaying the network diagram to the user via the display device;

receiving selection of the node included in the network diagram from the user via the input device; and additionally displaying character information or a diagram relating to a biological function of a group corresponding to the selected node, a diagram indicating a name, a sign, a structure or a composition of a biological material included in the group corresponding to the selected node, or character information relating to the biological material in the network diagram, wherein the plurality of biological materials are divided into a plurality of groups on the basis of a similarity of temporal variations of time-series data of the respective biological materials and a similarity of biological functions of the respective biological materials, wherein in a case where the plurality of biological materials are divided into the plurality of groups, at least one biological material is allowed to belong to a plurality of groups, and wherein in a case where the dependency between the groups is estimated, representative time-series data of each group is expressed as a function of representative time-series data of another group.

2. The biological material analysis system according to claim 1, wherein the similarity of the biological functions of the respective biological materials is evaluated on the basis of a gene ontology of each biological material, a canonical passway of each biological material, an upstream factor of each biological material, an expression system of each biological material, or a disease relating to each biological material.

3. The biological material analysis system according to claim 1, the process further comprising:

preparing a plurality of pieces of reference time-series data in advance; and comparing the plurality of pieces of reference time-series data with the time-series data of the respective biological materials to divide the plurality of biological materials into the plurality of groups.

4. The biological material analysis system according to claim 1, wherein in a case where the dependency between the groups is estimated, a value of the representative time-series data of each group at a first time point is set as a function of a value of the representative time-series data of the other group at a second time point before the first time point.

5. The biological material analysis support system according to claim 1, wherein in a case where the dependency between the groups is estimated, the representative time-series data of each group is expressed as a conditional probability or a conditional probability density function of the representative time-series data of the other group.

6. The biological material analysis system according to claim 1, wherein the representative time-series data of each group is set as an average value, a median value, a mode, a variance, a standard deviation, or a triple or higher moment of values of time-series data of biological materials that belong to each group at respective time points.

7. The biological material analysis system according to claim 1, wherein a value indicating the amount of the biological material is a value indicating an expression level, an existence amount, a concentration, or a density of the biological material, and wherein the network diagram is displayed to the user via the display device.

8. The biological material analysis system according to claim 1, wherein a value indicating the state of the biological material is a value indicating the presence or absence of expression of the biological material, a value indicating the presence or absence of existence thereof, a value indicating the presence or absence of chemical modification thereof, or a value indicating a ratio between biological materials having chemical modification and biological materials without chemical modification.

9. The biological material analysis system according to claim 1, wherein the plurality of biological materials include at least one of deoxyribonucleic acid (DNA), ribonucleic acid (RNA), protein, or low molecular compounds in vivo.

10. The biological material analysis system according to claim 1, wherein the plurality of biological materials are divided into a plurality of groups on the basis of a similarity of temporal variations of time-series data of the respective biological materials and each of the plurality of groups are further divided into a plurality of further groups based on a similarity of biological functions of the respective biological materials.

11. A biological material analysis system comprising:

a biological material analysis device comprising:

an input device;

a storage device that stores time-series data formed by acquiring values, from a user via the input device or from the storage device indicating amounts or states of a plurality of biological materials for each of the biological materials at a plurality of time points;

a classifier that divides the plurality of biological materials into a plurality of groups on the basis of a temporal variation of time-series data of each of the biological materials;

a dependency estimator that generates representative time-series data indicating the state of each group on the basis of time-series data of at least one biological material included in each group, and estimates a dependency between the groups on the basis of the representative time-series data of each group;

a controller generating a network diagram in which the respective groups are expressed as nodes and nodes corresponding to groups having the dependency are connected through edges, and a display device that displays the network diagram to the user via the display device, wherein the input device receives, from the user, selection of the node included in the network diagram;

wherein the display device additionally displays character information or a diagram relating to a biological function of a group corresponding to the selected node, a diagram indicating a name, a sign, a structure or a composition of a biological material included in the group corresponding to the selected node, or character information relating to the biological material in the network diagram, wherein the plurality of biological materials are divided into a plurality of groups on the basis of a similarity of temporal variations of time-series data of the respective biological materials and a similarity of biological functions of the respective biological materials, wherein in a case where the plurality of biological materials are divided into the plurality of groups, at least one biological material is allowed to belong to a plurality of groups, and wherein in a case where the dependency between the groups is estimated, representative time-series data of each group is expressed as a function of representative time-series data of another group.

12. A non-transitory computer-readable storage medium storing a biological material analysis program for causing a computer in a biological material analysis system comprising a biological material analysis device having the computer, a storage device, an input device, and a display device, to execute:

a step of storing time-series data formed by acquiring values, from a user via the input device or from the storage device, indicating amounts or states of a plurality of biological materials for each of the biological materials at a plurality of time points;

a step of dividing the plurality of biological materials into a plurality of groups on the basis of a temporal variation of the time-series data of each of the biological materials;

a step of generating representative time-series data indicating a state of each group on the basis of the time-series data of at least one biological material included in each group, and estimating a dependency between the groups on the basis of the representative time-series data of each group;

a step of generating a network diagram in which the respective groups are expressed as nodes and nodes corresponding to groups having the dependency are connected through edges, a step of displaying the network diagram to the user via the display device, a step of receiving selection of the node included in the network diagram from the user via the input device; and a step of additionally displaying character information or a diagram relating to a biological function of a group corresponding to the selected node, a diagram indicating a name, a sign, a structure or a composition of a biological material included in the group corresponding to the selected node, or character information relating to the biological material in the network diagram, wherein the plurality of biological materials are divided into a plurality of groups on the basis of a similarity of temporal variations of time-series data of the respective  5 biological materials and a similarity of biological functions of the respective biological materials, wherein in a case where the plurality of biological materials are divided into the plurality of groups, at least one biological material is allowed to belong to a plurality of  10 groups, and wherein in a case where the dependency between the groups is estimated, representative time-series data of each group is expressed as a function of representative time-series data of another group.  15

\*   \*   \*   \*   \*